United States Patent
Brown

(10) Patent No.: US 6,294,585 B1
(45) Date of Patent: *Sep. 25, 2001

(54) TREATMENT OF NEURODEGENERATIVE DISEASES

(75) Inventor: David A. Brown, Ellicott City, MD (US)

(73) Assignee: Applied Genetics Incorporated Dermatics, Freeport, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 37 days.

(21) Appl. No.: 08/933,145

(22) Filed: Sep. 18, 1997

Related U.S. Application Data

(60) Provisional application No. 60/048,957, filed on Jun. 4, 1997, provisional application No. 60/036,863, filed on Feb. 4, 1997, provisional application No. 60/035,947, filed on Jan. 21, 1997, and provisional application No. 60/026,577, filed on Sep. 18, 1996.

(51) Int. Cl.$^7$ .................................................. A61R 31/045

(52) U.S. Cl. .......................... 514/729; 514/724; 514/739; 514/548; 514/623

(58) Field of Search .................................. 514/724, 729, 514/739, 548, 643

(56) References Cited

U.S. PATENT DOCUMENTS

| | | |
|---|---|---|
| 3,956,361 | 5/1976 | Stephen . |
| 4,647,585 | 3/1987 | Loots et al. . |
| 5,130,136 | 7/1992 | Shono et al. . |
| 5,414,019 | 5/1995 | Gould et al. . |
| 5,587,402 | 12/1996 | Gould et al. . |
| 5,602,184 | 2/1997 | Myers et al. . |
| 5,747,532 * | 5/1998 | Lai ........................................ 514/305 |
| 5,990,177 | 11/1999 | Brown . |

FOREIGN PATENT DOCUMENTS 1 200 862    8/1970    (GB) .

OTHER PUBLICATIONS

Muck Index, 10th Edn, #1708, 2896, 3744, 7756, 9522, 1983.*

Bradford, M. "A Rapid and Sensitive Method for the Quantitation of Mictogram Quantities of Protein Utilizing the Principle of Protein–Dye Binding," *Anal. Biochem.*, 1967, 72:248–254.

Buchbauer et al., "Norbornanaverbindungen in der pharmazeutischen Forschung," *Pharmazie*, 1991, 46(Teil 1):88–97, and 46 (Teil 2):116–170.

Buchbauer et al., "Syntheses in the isocamphane series," *Chemical Abstracts*, vol. 95, NO. 115756e, 1981.

Chijiwa et al., "Inhibition of Forskolin–induced Neurite Outgrowth and Protein Phosphorylation by a Newly Synthesized Selective Inhibitor of Cyclic AMP–dependent Protein Kinases, N–[2– (p–Bromocinnamyl–amino) ethyl] 5–isoquinolinesulfonamide (H–89), of PC12D Phenochromocytoma Cells," *J. Biol. Chem.*, 1990, 265:5267–5272.

Crowell et al., "Chemoprevention of mammary carcinogenesis by hydroxylated derivatives of d–limonene," *Carcinogenesis*, 1992, 13:1261–1264.

Crowell et al., "Structure–activity relationships among monoterpene inhibitors of protein isoprenylation and cell proliferation," *Biochemical Pharmacology*, 1994, 47:1405–1415.

Durham et al., "Use of tissue culture models to study environmental–genetic interactions relevant to neurodegenerative diseases," *Clin. Exp. Pharmacol. Physiol.*, 1995, 22:366–67.

Greene et al., "Methodologies for the culture and experimental use of the rat PC12 rat pheochtomocytoma cells line," *Culturing Nerve Cells*, The MIT Press, Cambridge, Massachusetts, 1991, pp. 207–226.

Groner et al., "Cell damage by excess CuZnSOD and Down's Syndrome," *Biomed. Pharmacother.*, 1994, 48:231–240.

Haag et al., "Mammary carcinoma regression induced by perillyl alcohol, a hydroxilated analog of limonene," *Cancer Chemotherapy and Pharmacology*, 1994, 34:477–483.

Haase et al., "Gene therapy of murine motor neuron disease using adenoviral vectors for neurothrophic factors," *Nature Medicine*, 1997, 3:429–436.

He et al., "Isoprenoids Suppress the Growth of Murine B16 Melanomas In Vitro and In Vivo," *J. Nutr.*, 1997, 127:668–674.

Ishida et al., "Biotransformation of terpenoids in mammals," *Chemical Abstracts*, vol. 93, #89860W, 1980.

Jager et al., "Investigation of cytotoxic effects of 8 norbornane derivatives on 4 human cancer cell lines using the MTT assay," *Pharmazie*, 1995, 50:619–621.

Kamikubo et al., "Preparation of (+)—tricycloen–3–one and its conversion into (+) –epi–β–santalene," *Chemical Abstracts*, vol. 122, No. 265669u, 1994.

Karg et al., "Stimulation of Tyrosinase by Dihydroxy Phenyl Derivatives," *Acta Derm. Venereol.*, 1989, 69:521–524.

Koval'skaya et al., "Determination of the spatial structure of mono– and bicyclic terpene derivatives on the base of nuclear magnetic resonance spectroscopy data," *Chemical Abstracts*, vol. 125, No. 276201y, 1996.

Kozlov et al., "Camphene in the synthesis oxygen– and nitrogen–containing bicyclic derivatives," *Chemical Abstracts*, vol. 120, No. 77469p, 1994.

(List continued on next page.)

Primary Examiner—James H Reamer
(74) Attorney, Agent, or Firm—Maurice M. Klee

(57) ABSTRACT

Disclosed are methods for increasing the differentiation of mammalian neuronal cells for purposes of treating neurodegenerative diseases or nerve damage by administration of various compounds including alcohols, diols and/or triols and their analogues.

20 Claims, 1 Drawing Sheet

OTHER PUBLICATIONS

Laukharanta et al., "Changes in Three–Dimensional Structure of Cultured S91 Mouse Melanoma Cells Associated with Growth Inhibition and Induction of Melanogenesis by Retinoids," *Arch. Dermatol. Res.*, 1985, 277:147–150.

Merkel, D. "10–Methylenetricyclene," *Chemical Abstracts*, vol. 66, No. 94723a, 1967.

Michel et al., "Morphological and Molecular Characterization of the Response of Differentiated PC12 Cells to Calcium Stress," *Europ. J. Neurosci. Assoc.*, 1994, 6:577–586.

Miftakhov et al., "Prostanoids," *Chemical Abstracts*, vol. 121, No. 157329d, 1994.

Nagatsu et al., "A Rapid and Simple Radioassay for Tyrosine Hydroxylase Activity," *Anal. Biochem.*, 1969, 9:122–126.

Ribeiro et al., "The Hydroxylation of Phenylalanine and Tyrosine by Tyrosine Hydroxylase from Cultured Pheochromocytoma Cells," *J. Biol. Chem.*, 1991, 16207–16211.

Riederer et al., "Recent Advances in Pharmacological Therapy of Parkinson's Disease," *Adv. Neurol.*, 1993, 60:626–635.

Romero et al., "Retinoic acid as modulator of UVB–induced melanocyte differentation," *J. Cell Sci.*, 1994, 107:1095–1103.

Rukenstein et al., "Multiple Agents Rescue PC12 Cells from Serum–free Cell Death by Translation– and Transcription–independent Mechanisms," *J. Neurosci.*, 1991, 11:2552–2563.

Russin et al., "Inhibition of rat mammary carcinogenesis by monoterpenoids," *Carcinogenesis*, 1989, 10:2161–2164.

Sandrock et al., "Identification of a peripheral nerve neurite grwoth–promoting activity by development and use of an in vitro bioassay," *Proc. Natl. Acad. Sci. U.S.A.*, 1987, 84:6934–6938.

Shen et al., "Complement–mediated neurotoxcity is regulated by homologus restritction," *Brain Res.*, 1995, 671:282–292.

Shi et al., "Induction of differentiation in neuro–2A cells by the monoterpene perillyl alcohol," *Cancer Letters 95*, 1995, 1–6.

Shoff et al., "Concentration–dependent Increase of Murine P388 and B16 Population Doubling time by the Acyclic Monoterpene Geraniol," *Cancer Research*, 1991, 41:37–42.

Steiner et al. "Neurotrophic actions of nonimmuno–suppressive analogues of immunosuppressive drugs FK506, rapamycin and cyclosporin A," *Nature Medicine*, 1997, 3:421–428.

Taglialatela et al., "Suppression of p140$^{trkA}$ Does Not Abolish Nerve Growth Factor–Mediated Rescue of Serum–Free PC12 Cells," *J. Neurochem.*, 1996, 66:1826–1835.

Uchida et al., "Electrochemical oxidation of polycyclic cyclopropanes and camphene," *Chemcial Abstracts*, vol. 112, No. 198816t, 1990.

Yahr, M. D., "Parkinson's Disease: The L–DOPA Era," *Adv. Neurol.*, 1993, 60:11–17.

\* cited by examiner

TREATMENT OF NEURODEGENERATIVE DISEASES

CROSS REFERENCE TO RELATED APPLICATIONS

This application is a continuation-in-part of application Ser. No. 60/026,577 filed Sep. 18, 1996, of application Ser. No. 60/035,947 filed Jan. 21, 1997, of application Ser. No. 60/036,863 filed Feb. 4, 1997, and of application Ser. No. 60/048,597 filed Jun. 4, 1997.

STATEMENT REGARDING FEDERALLY SPONSORED RESEARCH OR DEVELOPMENT

Not Applicable

BACKGROUND OF THE INVENTION

1. Field of the Invention

The present invention relates to increasing the differentiation of mammalian neuronal cells for purposes of treating neurodegenerative diseases or nerve damage by administration of various compounds including alcohols, diols and/or triols and their analogues.

2. Description of Related Art

The compositions which are the subject of the present invention have been found to increase the melanin content of mammalian melanocytes, increase pigmentation in the epidermis of a mammal, and treat or prevent various skin and proliferative disorders. See U.S. application Ser. No. 60/026,577 filed Sep. 18, 1996; application Ser. No. 60/035,947 filed Jan. 21, 1997; application Ser. No. 60/036,863 filed Feb. 4, 1997, and application Ser. No. 60/048,597 filed Jun. 4, 1997. It has now been found that the present compositions may be used for treating neurodegenerative diseases or nerve damage.

SUMMARY OF THE INVENTION

The present invention provides a method for increasing the differentiation of mammalian neuronal cells, which comprises administering to a mammal in need of such increase an effective amount of one or more compounds having the following structure:

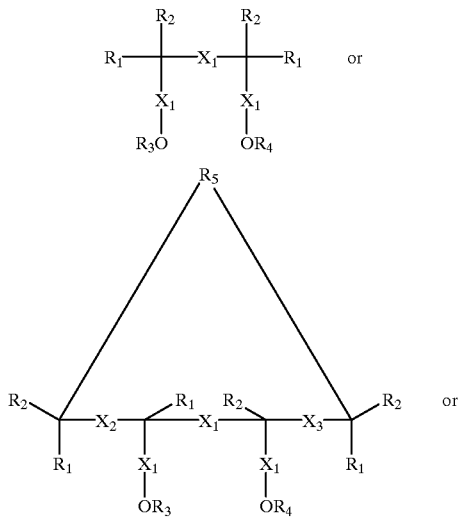

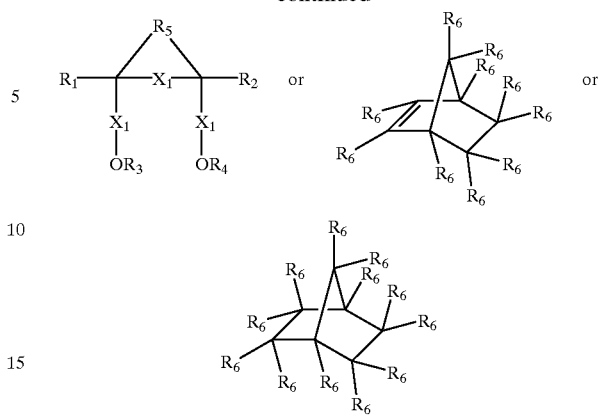

wherein
  $X_1$, $X_2$, and $X_3$ are independently selected from a single bond; or a group containing from one atom to twenty atoms, at least one of which is carbon, nitrogen, oxygen or sulfur;
  each of $R_1$ and $R_2$ is independently selected from hydrogen; halogen; or a group containing from one atom to twenty atoms, one of which is carbon, nitrogen, oxygen, or sulfur;
  each of $R_3$ and $R_4$ is independently selected from hydrogen or an acyl or amino acyl group containing from one atom to twenty atoms, at least one of which is carbon, nitrogen, oxygen, or sulfur;
  $R_5$ is a linear, branched or unbranched, cyclic, bicyclic or polycyclic group containing from one atom to fifty atoms, at least one of which is carbon, nitrogen, oxygen, or sulfur, and
  each $R_6$ is independently selected from hydrogen; halogen; or a group containing from one atom to twenty atoms, one of which is carbon, nitrogen, oxygen, or sulfur; hydroxyl, hydroxymethyl, $—(CH_2)_nOH$, $—(CH_2)_nOR_1$, $—(CH_2)_n—CH(OH)—CHOH$, $—(CH_2)_n—CH(OH)—CH(OH)R_1$, $—(CH_2)_n—CH(OH)—(CH_2)_n—CH_2(OH)$, $—(CH_2)_n—CH(OH)—(CH_2)_n—CH(OH)R_1$ or $—CH_2OR_3$, wherein each n is independently an integer from 0–25;
  and pharmaceutically acceptable salts thereof In another aspect, the present invention provides a composition for increasing the differentiation of mammalian neuronal cells, which comprises:
  a) an effective amount of one or more compounds described above; and
  b) a suitable carrier.

DETAILED DESCRIPTION OF THE INVENTION

Figure 1A:
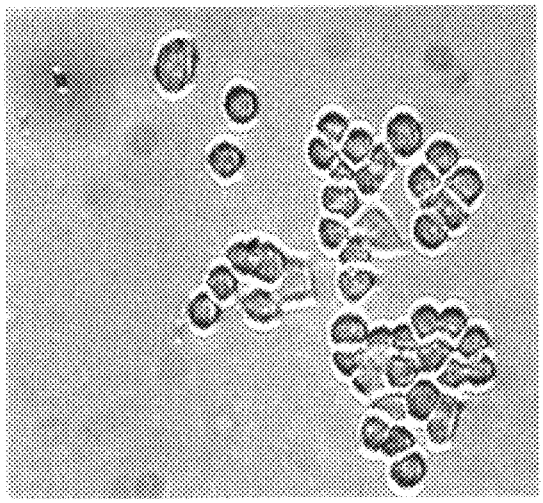
FIGS. 1A–1B are photographs as described in Example 1.

The present invention is based on the unique observation that certain compounds effectively and efficiently increase differentiation of neuronal cells, including increased neuronal dendricity and neuronal tyrosine hydroxylase activity, which has several consequences. First, increasing dendricity leads to increased neuronal communication, thereby increasing neuronal function and performance. Thus, the present invention is useful for treating diseases or disorders marked by reduction of neuronal dendricity and function, including but not limited to Parkinson's disease, amyotrophic lateral sclerosis, Alzheimer's disease, or any other neurodegenerative disease, or physical or toxic damage to brain, spinal or peripheral nerve cells. Further, the present invention is useful for restoring or optimizing neuronal communication, function or performance.

Second, increasing tyrosine hydroxylase activity directly increases dopamine synthesis. Thus, the present invention is particularly useful for treating Parkinson's disease which is specifically marked by depletion of dopamine synthesis.

Third, induction of neuronal differentiation reverses neuronal proliferative disorders. Thus, the present invention is useful for treating neuronal proliferative, tumorous, or cancerous disorders, or said disorders in any other cell type that might be similarly affected.

Finally, since the methods and compositions described herein induce differentiation, dendricity and tyrosine hydroxylase in a neuronal cell model, the present invention is useful for treating additional neurodegenerative disorders or neuropathies including but not limited to diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, and ophthalmoplegia.

The active compounds according to the present invention have the structures described above. More preferably, each X is independently selected from a single bond; or $C_1$–$C_{10}$ alkylene, $C_2$–$C_{10}$ alkenylene, or $C_2$–$C_{10}$ alkynylene, each of which may contain one or more different heteroatoms or heteroatoms of the same type. More preferably each of $R_1$ and $R_2$ is independently selected from hydrogen; fluoro; chloro; or $C_1$–$C_{20}$ alkyl, $C_2$–$C_{20}$ alkenyl, $C_2$–$C_{20}$ alkynyl, $C_7$–$C_{20}$ aralkyl, $C_8$–$C_{20}$ aralkenyl, $C_8$–$C_{20}$ aralkynyl, or $C_6$–$C_{20}$ aryl, each of which may contain one or more different heteroatoms or heteroatoms of the same type, or carboxyl, carboxamido, carbalkoxy, sulfamido, sulfonamido; hydroxyl, or amino. More preferably each of $R_3$ or $R_4$ is independently selected from hydrogen or $C_1$–$C_{18}$ acyl, which may contain one or more different heteroatoms or heteroatoms of the same type. More preferably $R_5$ contains from two to twenty carbon atoms, each may contain one or more different heteroatoms or heteroatoms of the same type.

The preparation of the present compounds would be apparent to one of ordinary skill, and many of them are commercially available. Representative preferred compounds include, but are not limited to:

1,2-Ethanediol
1,2-Propanediol (Propylene Glycol)
(S)-(+)-1,2-Propanediol [(S)-(+)-1,2-Propylene Glycol]
1,3-Propanediol
2,3-Dimethyl-2,3-Butanediol
2,3-Dimethyl-1,2-Butanediol
1-Phenyl-1,2-Propanediol
2-Methyl-1,3-Propanediol
1,2-Butanediol
1,3-Butanediol
1,4-Butanediol
2,3-Butanediol
(2R,3R)-(−)-2,3-Butanediol
(2S,3S)-(+)-2,3-Butanediol
2,3-meso-Butanediol
1,2-Pentanediol
1,4-Pentanediol
1,5-Pentanediol
2,4-Pentanediol
1,2-cis-cyclopentanediol
1,2-trans-cyclopentanediol
1,2-cis-cyclohexaneanediol
1,2-trans-cyclohexanediol
1,2-dihydroxy-4,5-cyclohexanediol carbonate
1,2,4,5-tetrahydroxycyclohexane
1,2-Hexanediol
1,5-Hexanediol
1,6-Hexanediol
2,5-Hexanediol
1,2-Heptanediol
1,7-Heptanediol
7-Octene-1,2-diol
1,2-Octanediol
1,8-Octanediol
1,2-Nonanediol
1,9-Nonanediol
1,2-Decanediol
1,10-Decanediol
1,2-Dodecanediol
1,12-Dodecanediol
1,2-Tetradecanediol
1,14-Tetradecanediol
1,2-Hexadecanediol
1,16-Hexadecanediol
Glycerol
1,2,4-Butanetriol
1,2,3-Trihydroxyhexane
1,2,6-Trihydroxyhexane
1,2,3-Heptanetriol
β-estradiol
azabicyclo-(2,2,1)-heptanediol-3-one
1,4-dioxane-2,3-diol
5-norbornene-2,2-dimethanol
norbornane-2,2-dimethanol
2,3-norbornanediol (exo or endo or cis or trans)
2,3-cis-exo-norbornanediol
α-norborneol
2-norbornanemethanol
norbornane
borneol
camphor
camphene
camphane
norbornane acetic acid
norbornane-carboxylic acid
norbornane-dicarboxylic acid
2-endo-hexadecylamino-5-norbornene-2-exo-methanol
2-endo-hexadecylamino-5-norbornene-2,3-exo-dimethanol
2-(propyl-1,2-diol)-norbornane
1,2-dithiane-trans-4,5-diol
2,3-pyridinediol
2,3-pyridinediol hydrogen chloride 2,3-pyridinediol glycolic acid
2,3-dipyridyl-2,3-butanediol
2,2,4,4-tetramethyl-1,3-cyclobutanediol Particularly preferred compounds of this invention are 5-norbornene-2,2-dimethanol; norbornane-2,2-dimethanol; 2-norbornanemethanol; 1,2-cis-cyclopentanediol; 2,3-cis-exo-norbornanediol, 2-(propyl-1,2-diol)-norbornane and 3,3-dimethyl-1,2-butanediol. Other preferred compounds are 1,2-trans-cyclopentanediol; 2,3-dimethyl-2,3-butanediol; 2-methyl-1,3-propanediol; 2,3-butanediol; and propylene glycol.

The methods and compositions of the present invention contemplate the use of one or more of the above-mentioned compounds as an active ingredient to stimulate neuronal differentiation, dendricity, and/or tyrosine hydroxylase activity (with resultant increased dopamine synthesis). In a preferred embodiment, the active ingredient(s) is given orally, intravenously, or transdermally in an acceptable formulation. A particularly preferred carrier for some formulations is 1,2-propylene glycol since it is an excellent solvent for certain compounds in this invention including but not limited to 5-norbornene-2,2-dimethanol, 5-norbornane-2,2-dimethanol and 3,3-dimethyl-1,2-butanediol. Additionally, 1,2-propylene glycol as carrier has itself, as described in this invention, similar but lessor activity than the preferred active ingredient(s). Depending on the specific application, the compositions of the present invention may also include other active ingredients, as well as inert or inactive ingredients.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 100 mg of active ingredient, preferably about 0.1 mg to about 10 mg of active ingredient. Topical formulations (such as creams, lotions, solutions, etc.) may have a concentration of active ingredient of from about 0.01% to about 50%, preferably from about 0.1% to about 10%.

The use of and useful and novel features of the present methods and compositions will be further understood in view of the following non-limiting examples.

EXAMPLE 1

The PC12 rat pheochromocytoma cell line was obtained from American Type Culture Collection (ATCC). Cells were cultured in 85% RPMI 1640 medium, 10% horse serum (heat inactivated at 56° C. for 30 minutes, 5% fetal bovine serum, 25 U/ml penicillin, and 25 ug/ml streptomycin (Greene, et al., 1991, "Methodologies for the culture and experimental use of the rat PC12 rat pheochromocytoma cells line", pp. 207–225, In: Culturing Nerve Cells, The MIT Press, Cambridge, Mass.). Cells were cultured directly on plastic dishes at 37° C. in 5% $CO_2$ in a humidified incubator.

PC12 rat pheochromocytoma cells are considered to be an excellent model for neuronal cells because they respond to treatment with nerve growth factor (NGF) by acquisition of a number of properties of neurons including cessation of proliferation, extension of neurons, acquisition of electrical excitability, and increased neurotransmitter synthesis (Greene, et al., 1991 and references therein). In addition, PC12 cells are used as a model for studies of prevention or cure of neurodegenerative diseases since they provide a robust screen for agents that maintain neuron survival and prevent neuron cell death in serum-free media (Rukenstein, et al., 1991, J. Neurosci. 11:255–2563). Agents are considered to be potentially useful for treatment of neurodegenerative disorders if they not only promote PC12 cell survival, but also increase neurite outgrowth (Rukenstein, et al., 1991). Agents are considered to be particularly useful for treatment of neurodegenerative disorders if they promote PC12 cell survival and neurite outgrowth in the absence of "priming" with NGF (Rukenstein, et al., 1991). By virtue of their ability to express tyrosine hydroxylase and thereby synthesize dopamine, PC12 cells are considered to be an especially good model for studies of Parkinson's disease (Michel, et al., 1994, Europ. J. Neurosci. Assoc. 6:577–586 and references therein). In addition, neurite outgrowth in PC12 cells has been used to identify agents that stimulate the regeneration of severed neuronal axons in the peripheral nerves of adult mammals (Sandrock, A. W. and Matthew, W. D., 1987, Proc. Natl. Acad. Sci. U.S.A. 84:6934–6938). Moreover, PC12 cells have been used as a model to study aspects of Alzheimer's disease (Shen, et al., 1995, Brain Res. 671:282–292), amyotrophic lateral sclerosis (Durham, et al., 1995, Clin. Exp. Pharmacol. Physiol. 22:366–67), Down's syndrome (Groner, et al., 1994, Biomed. Pharmacother. 48:231–240), and age-related neurodegeneration (Taglialatela, et al., 1996, J. Neurochem. 66:1826–1835).

For testing compounds for induction of dendricity (neurite outgrowth) and tyrosine hydroxylase activity in this invention, cells were plated at 15,000 cells/35 mm dish. Two days following plating, cell culture media was replaced with that containing treatments. One week later, media and treatments were replaced with fresh media and treatments. Two weeks following the initial treatments, cells were examined microscopically, and the portion of cells exhibiting dendricity was estimated. Cells were harvested by trypsinization and counted by Coulter Counter. Cells were pelleted by centrifugation at 200×g, and cell pellets were lysed in 600 ul 50 mM Tris/Acetate pH 6.0/0.2% Triton X-100 by vortexing, sonicating 5 seconds, incubating on ice for 30 minutes, followed by revortexing. Protein was determined on aliquots of cell lysate by the Bradford Coomassie Blue method (Bradford, 1967, Anal. Biochem. 72:248–254) using Bio-Rad Protein Assay Kit I. Tyrosine hydroxylase activity was determined by incubating 100 ul of PC12 cell lysate with 100 ul of the following reaction mixture at 37° C. for 15 min: 200 mM sodium acetate pH 6.0, 50 uM tyrosine, 2000 U Cat/ml, 50 mU dihydropteridine reductase/ml, 0.1 mM NADH final, 200,000 cpm 3H tyrosine/100 ul, 0.1 mM NSD1015 (3-hydroxybenzylhydrazine), and 100 uM tetrahydrobiopterin (BH4) (Nagatsu, et al., 1969, Anal. Biochem. 9:122–126; Ribeiro, et al. 1991, J. Biol. Chem. 16207–16211). Reactions were stopped by addition of 200 ul 10% activated charcoal in 0.1N HCl and incubation on ice for 15 min. This mixture was centrifuged at 17,300×g for 5 min, and 200 ul supernatant was then filtered through a 0.22 uM GV Durapore centrifugal filter unit (Millipore) by centrifuging at 17,300×g for 5 min. Filtrate was added to 4 ml Fisher Plus scintillation fluid and counted on a Hewlett Packard scintillation counter. Tyrosine hydroxylase activity was measured as tritium release and was calculated as dpm/ug protein and dpm/$10^3$ cells per hour.

Figure 1B:
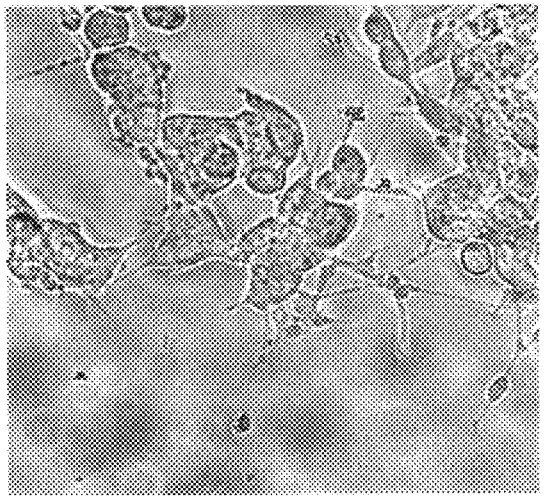

Microscopic examination showed that a large portion of PC12 cells treated with 5 mM 5-norbornene-2,2-dimethanol (5-NBene-2,2-DM) acquired dendritic processes (Table 1, and compare untreated PC12 cells in FIG. 1A with 5-NBene-2,2-DM treated PC12 cells in FIG. 1B). Lesser increases of dendritic processes were noted following treatment with 3,3-dimethyl-1,2-butandiol (3,3-M-1,2-BD) or 1,2-propylene glycol (1,2-PG) (Table 1). The most notable increases of tyrosine hydroxylase activity resulted from treatment with 25 mM 3,3-M-1,2-BD and 5 mM 5-NBene-2,2-DM (Table 1). Treatment with 1,2-PG, 3,3-M-1,2-BD and 5-NBene-2,2-DM increased the amount of protein per cells, a feature often associated with induction of differentiation. Increases of protein per cells were manifested morphologically as an increase in cell size (compare untreated PC12 cells in FIG. 1A with 5-NBene-2,2-DM treated PC12 cells in FIG. 1B). Examination of the data in Table 1 shows that increases of tyrosine hydroxylase per cell as a result of treatment with 1,2-PG, 3,3-M-1,2-BD or 5-NBene-2,2-DM, were in part, a result of increases of the amount of protein per cell. Ethanol (ETOH), used as a solvent for 3,3-M-1,2-BD and 5-NBene-2,2-DM, and IBMX (3-isobutly-1-methylxanthine), which increases cellular cAMP levels, resulted in only minor effects relative to the agents of this invention.

It should be particularly noted that the compounds of this invention induced dendricity and tyrosine hydroxylase activity in the absence of priming with NGF, a prerequisite for induction of neurite extension by many other agents tested on PC12 cells (Steiner, et al. 1997, Nature Medicine 3:421–428; Rukenstein, et al. 1991, J. Neurosci. 11:2552–2563). Several agents under consideration as treatments for neurodegenerative diseases do not promote neurite extension even in NGF-primed PC12 cells (e.g., IGF-I and IGF-II; Rukenstein, et al., 1991 and references therein). Moreover, many agents under consideration for treatment of neurodegenerative diseases including GDNF (glial cell-derived neurotrophic factor) being developed for treatment of Parkinson's disease are neurotrophic peptides that cannot cross the blood-brain barrier and therefore require gene therapy implantation at the site of action (Haase, et al. 1997, Nature Medicine 3:429–436). Furthermore, L-Dopa which is presently used for treatment of Parkinson's disease is toxic (Yahr, M. D. 1993, Adv. Neurol. 60:11–17), in part, by generation of peripherally formed dopamine (Riederer, et al. 1993, Adv. Neurol. 60:626–635), and in part, by virtue of its

TABLE 1

|  | Cells/Dish (×10³) | % Dendritic | ug Protein/ 10³ Cells | dpm/hr Tyrosine Hydroxylase /10³ Cells | Tyrosine Hydroxylase /ug Protein |
| --- | --- | --- | --- | --- | --- |
| Untreated | 0.728 | 1% | 0.47 | 3708 | 7888 |
| Untreated | 0.490 | 1% | 0.61 | 4812 | 7888 |
| Mean Untreated | 0.609 | 1% | 0.54 | 4260 (1.00×) | 7888 (1.00×) |
| 17 mM ETOH (0.1%) | 0.410 | 2% | 0.78 | 7344 (1.72×)[1] | 9416 (1.19×) |
| 85 mM ETOH (0.5%) | 0.367 | 5% | 0.82 | 7308 (1.72×) | 8912 (1.13×) |
| 100 mM 1,2-PG | 0.180 | 10% | 1.66 | 12988 (3.05×) | 7824 (0.99×) |
| 300 mM 1,2-PG | 0.197 | 2% | 1.57 | 16152 (3.79×) | 10288 (1.30×) |
| 10 mM 3,3-M-1,2-BD | 0.214 | 25% | 1.11 | 8828 (2.07×) | 7952 (1.01×) |
| 25 mM 3,3-M-1,2-BD | 0.044 | 5% | 2.22 | 37148 (8.72×) | 16732 (2.12×) |
| 5 mM 5-NBene-2,2-DM | 0.155 | 50% | 1.64 | 28956 (6.80×) | 17656 (2.23×) |
| 10 mM 5-NBene-2,2-DM | 0.010 | 25% | 2.33 | 12732 (3.00×) | 5464 (0.69×) |
| 0.1 mM IBMx | 0.346 | 2% | 1.20 | 9148 (2.15×) | 7624 (0.97×) |

[1]Fold increase relative to mean untreated control value.

The reduced cell numbers resulting from treatment with 1,2-PG, 3,3-M-1,2-BD or 5-NBene-2,2-DM are in part indicative of the differentiation process induced by treatments. However, in the case of treatment with 25 mM 3,3-M-1,2-BD and 10 mM 5-NBene-2,2-DM, some cells detached concomitantly with the acquisition of dendricity that occurred earlier than for other treatments. This detachment phenomenon has been noticed previously for PC12 cells induced to differentiate with NGF, and can be avoided by coating treatment dishes with collagen (reviewed in Greene, et al., 1991). Treatment with collagen also shortens the time required for dendrite formation and greatly increases the extent of dendrite formation in response to treatment with NGF (reviewed in Greene, et al., 1991). Thus, it is contemplated that the compounds of this invention will prove to exhibit more activity when tested on collagen-coated dishes.

Induction of differentiation as indicated by induction of dendricity, induction of tyrosine hydroxylase activity, increased cellular protein levels and induction of cell cycle arrest as indicated by reduced growth, indicate that the compounds of this invention can act as chemotherapeutic agents for treatment of neural tumorous and cancerous disorders and additional neural proliferative disorders. In addition, it is contemplated that the compounds of this invention will treat tumorous, cancerous and proliferative disorders arising from additional cell types.

ability to form highly reactive semiquinone and quinones via autooxidation (Karg, et al. 1989, Acta Derm. Venereol. 69:521–524). Given that the agents of the present invention: (i) act directly without a requirement for NGF; (ii) induce neuronal differentiation thereby setting into motion cellular reprogramming to the desired phenotype; (iii) induce tyrosine hydroxylase, the rate-limiting enzyme in dopamine synthesis; (iv) are small molecule drugs that are likely to cross the blood brain barrier; and (v) have no known ability to form semiquinone, quinone or other toxic intermediates, it is contemplated that the agents of this invention will be particularly advantageous for treatment of neurodegenerative diseases including but not limited to Parkinson's disease.

What is claimed is:

1. A method for increasing the differentiation of mammalian neuronal cells to a statistically significant level above background, which comprises administering to mammalian cells in need of such increase a pharmaceutical composition comprising an effective amount of one or more diols having the following structure:

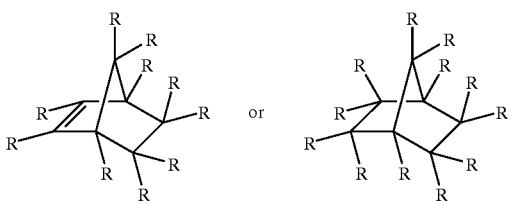

wherein
  each R is independently selected from hydrogen; halogen; a group containing from one atom to twenty atoms, one of which is carbon, nitrogen, oxygen, or sulfur; hydroxyl; hydroxymethyl; —$(CH_2)_nOH$; —$(CH_2)_nOR'$; —$(CH_2)_n$—CH(OH)—CHOH; —$(CH_2)_n$—CH(OH)—CH(OH)R'; —$(CH_2)_n$—CH(OH)—$(CH_2)_n$—$CH_2(OH)$; —$(CH_2)_n$—CH(OH)—$(CH_2)_n$—CH(OH)R'; or —$CH_2OR'$; wherein each n is independently an integer from 0–25;
  each R' is independently selected from hydrogen or an acyl or amino acyl group containing from one atom to twenty atoms, at least one of which is carbon, nitrogen, oxygen, or sulfur;
  or pharmaceutically acceptable salts thereof, and
  a pharmaceutically suitable carrier.

2. The method of claim 1, wherein the diol is selected from the group consisting of 5-norbornene-2,2-dimethanol, norbornane-2,2-dimethanol, 2,3-norbornanediol (exo or endo or cis or trans), 2,3-cis-exo-norbornanediol, and 2-endo-hexadecylamino-5-norbornene-2,3-exo-dimethanol.

3. The method of claim 2, wherein the diol is selected from 5-norbornene-2,2-dimethanol; norbornane-2,2-dimethanol; and 2,3-cis-exo-norbornanediol.

4. A pharmaceutical composition for increasing the differentiation of mammalian neuronal cells to a statistically significant level above background, which comprises:
  a) an effective amount of one or more diols having the following structure:

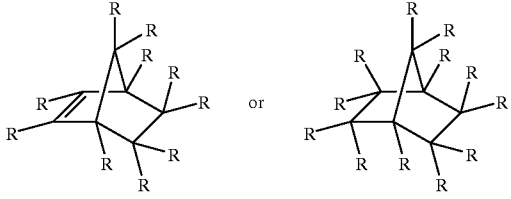

wherein
    each R is independently selected from hydrogen; halogen; a group containing from one atom to twenty atoms, one of which is carbon, nitrogen, oxygen, or sulfur; hydroxyl; hydroxymethyl; —$(CH_2)_nOH$, —$(CH_2)_nOR'$; —$(CH_2)_n$—CH(OH)—CHOH; —$(CH_2)_n$—CH(OH)—CH(OH)R'; —$(CH_2)_n$—CH(OH)—$(CH_2)_n$—$CH_2(OH)$; —$(CH_2)_n$—CH(OH)—$(CH_2)_n$—CH(OH)R'; or —$CH_2OR'$; wherein each n is independently an integer from 0–25;
    each R' is independently selected from hydrogen or an acyl or amino acyl group containing from one atom to twenty atoms, at least one of which is carbon, nitrogen, oxygen, or sulfur;
  or pharmaceutically acceptable salts thereof; and
  b) a pharmaceutically suitable carrier.

5. The composition of claim 4, wherein the diol is selected from the group consisting of 5-norbornene-2,2-dimethanol, norbornane-2,2-dimethanol, 2,3-norbornanediol (exo or endo or cis or trans), 2,3-cis-exo-norbornanediol, and 2-endo-hexadecylamino-5-norbornene-2,3-exo-dimethanol.

6. The composition of claim 5, wherein the diol is selected from 5-norbornene-2,2-dimethanol; norbornane-2,2-dimethanol; and 2,3-cis-exo-norbornanediol.

7. The method of claim 1, wherein the differentiation reverses neuronal damage.

8. The method of claim 1, wherein the differentiation alleviates a neurodegenerative disease.

9. The method of claim 8, wherein the disease is selected from the group consisting of Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, and ophthalmoplegia.

10. The method of claim 1, wherein the differentiation alleviates a cancerous, tumorous or proliferative disorder.

11. The method of claim 1 wherein the mammalian cells are a mammal.

12. The composition of claim 4 wherein the mammalian cells are a mammal.

13. The method of claim 1 wherein the increase in differentiation of neuronal cells is sufficient to form neurite outgrowth on PC12 cells in at least about 25% of the cells.

14. The composition of claim 4 wherein the increase in differentiation of neuronal cells is sufficient to form neurite outgrowth on PC12 cells in at least about 25% of the cells.

15. The composition of claim 4 wherein the differentiation reverses neuronal damage.

16. The composition of claim 4 wherein the differentiation alleviates a neurodegenerative disease.

17. The composition of claim 16 wherein the disease is selected from the group consisting of Parkinson's disease, amyotrophic lateral schlerosis, Alzheimer's disease, diffuse ceregral cortical atrophy, Lewy-body dimentia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum defoimans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hyupertrophic interstitial polyneuropathy, heredopathia atactica polyneuritiformis, optic neuropathy and ophthalmoplegia.

18. The composition of claim 4 wherein the differentiation alleviates a cancerous, tumorous or proliferative disorder.

19. The method of claim 1 wherein the composition is in a unitary dose.

20. The composition of claim 4 in a unitary dose.

* * * * *